US012364641B2

(12) United States Patent
Kim et al.

(10) Patent No.: US 12,364,641 B2
(45) Date of Patent: Jul. 22, 2025

(54) WALKING ASSISTING APPARATUS

(71) Applicants: Hyundai Motor Company, Seoul (KR); Kia Corporation, Seoul (KR)

(72) Inventors: Kyu Jung Kim, Seoul (KR); Hyun Seop Lim, Anyang-si (KR); Ju Young Yoon, Suwon-si (KR); Dong Jin Hyun, Suwon-si (KR); Sang In Park, Suwon-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 972 days.

(21) Appl. No.: 17/484,502

(22) Filed: Sep. 24, 2021

(65) Prior Publication Data

US 2022/0331189 A1 Oct. 20, 2022

(30) Foreign Application Priority Data

Apr. 16, 2021 (KR) .................. 10-2021-0050113

(51) Int. Cl.
*A61H 3/00* (2006.01)
*A61F 5/01* (2006.01)

(52) U.S. Cl.
CPC ............. *A61H 3/00* (2013.01); *A61F 5/0123* (2013.01); *A61F 2005/0155* (2013.01); *A61H 2003/007* (2013.01); *A61H 2201/0173* (2013.01); *A61H 2201/0192* (2013.01); *A61H 2201/1623* (2013.01); *A61H 2201/1628* (2013.01); *A61H 2201/163* (2013.01); *A61H 2201/1635* (2013.01); *A61H 2201/164* (2013.01); *A61H 2201/1642* (2013.01); *A61H 2201/165* (2013.01)

(58) Field of Classification Search
CPC ................................................. A61F 2005/0155
See application file for complete search history.

(56) References Cited

U.S. PATENT DOCUMENTS

| | | | |
|---|---|---|---|
| 9,808,073 B1 | 11/2017 | Maxwell et al. | |
| 9,868,204 B2 | 1/2018 | Seo et al. | |
| 10,137,050 B2 | 11/2018 | Goffer | |
| 2014/0196757 A1 | 7/2014 | Goffer | |
| 2015/0045703 A1 | 2/2015 | Strausser et al. | |

FOREIGN PATENT DOCUMENTS

| | | |
|---|---|---|
| JP | 2012183277 A | 9/2012 |
| JP | 5578036 B2 | 8/2014 |
| KR | 20150110633 A | 10/2015 |

*Primary Examiner* — David H Willse
(74) *Attorney, Agent, or Firm* — Slater Matsil, LLP

(57) ABSTRACT

A walking assisting apparatus includes a leg mounted device configured to be mounted on a leg of a user to assist walking of the user. A waist mounted device is provided on an upper side of the leg mounted device and configured to be mounted on a waist of the user. A support is located on a front side of the leg mounted device and configured to contact a ground surface. A control device is coupled to a front side of the waist mounted device, electrically connected to the leg mounted device, and configured to control the leg mounted device. A connector connects the control device and the leg mounted device to detachably house the support.

20 Claims, 11 Drawing Sheets

WALKING ASSISTING APPARATUS

CROSS-REFERENCE TO RELATED APPLICATIONS

This application claims the benefit of Korean Patent Application No. 10-2021-0050113, filed in the Korean Intellectual Property Office on Apr. 16, 2021, which application is hereby incorporated herein by reference.

TECHNICAL FIELD

The present disclosure relates to a walking assisting apparatus.

BACKGROUND

In general, a walking assisting apparatus that is mounted on a leg of a user and assists walking of the user includes a frame structure, a joint structure, and a battery.

A walking assisting apparatus according to the related art has a form in which a battery is located on the back of the user. As an example, the walking assisting apparatus has a form in which the battery is disposed on the back of the user and is mounted as a bag. According to the structure, because the center of weight of the walking assisting apparatus is moved rearward when the user wears the walking assisting apparatus, there is a possibility of a danger of a falling accident.

In addition, the walking assisting apparatus according to the related art has a structure in which it is balanced by gripping a clutch by the user. When the user balances by gripping the clutch, the weight of the user and a load of the walking assisting apparatus are fully delivered to an arm so that an excessive force is applied to the user because the user takes a standing posture, and the load applied to the walking assisting apparatus also increases.

SUMMARY

The present disclosure can solve problems occurring in the prior art while advantages achieved by the prior art are maintained intact.

An embodiment of the present disclosure provides a walking assisting apparatus that can prevent a danger of a falling accident, in which a user falls down rearwards, and reduce a burden of a load applied to the user.

According to an embodiment of the present disclosure, a walking assisting apparatus includes a leg mounted device mounted on a leg of a user to assist walking of the user, a waist mounted device provided on an upper side of the leg mounted device and mounted on a waist of the user, a support located on a front side of the leg mounted device and which contacts a ground surface, a control device coupled to a front side of the waist mounted device, electrically connected to the leg mounted device, and which controls the leg mounted device, and a connector connecting the control device and the leg mounted device and detachably housing the support.

According to an embodiment, the leg mounted device may include a first leg part coupled to the waist mounted device and extending downwards, and a second leg part located on a lower side of the first leg part, a length of which is adjustable, and connected to the first leg part to be rotatable.

According to another embodiment, the leg mounted device may further include a third leg part located on a lower side of the second leg part, a length of which is adjustable, and connected to the second leg part to be rotatable.

According to another embodiment, the leg mounted device may further include a foot seated part located on a lower side of the third leg part, connected to the third leg part to be rotatable, and configured such that a foot of the user is seated thereon, and a foot joint part configured such that the third leg part is elastically supported on the foot seated part.

According to another embodiment, the second leg part may include a (2-1)-th leg member connected to the first leg part to be rotatable and extending downwards from the first leg part, and a (2-2)-th leg member surrounding the (2-1)-th leg member and configured such that an extent of an area that overlaps the (2-1)-th leg member is variable.

According to another embodiment, the (2-1)-th leg member may include a first hole that is penetrated in one direction, the (2-2)-th leg member may include a second hole that is disposed at a location, which overlaps the first hole when viewed from one direction as the (2-2)-th leg member is moved along a vertical direction, and the second leg part may further include a fixing member that passes through the second hole and the first hole and which fixes the (2-2)-th leg member to a specific location of the (2-1)-th leg member.

According to another embodiment, the third leg part may further include a (3-1)-th leg member connected to the second leg part to be rotatable and extending downwards from the second leg part, a (3-2)-th leg member surrounding the (3-1)-th leg member and configured such that an extent of an area that overlaps the (3-1)-th leg member is variable, and a (3-3)-th leg member connected to the (3-2)-th leg member, disposed on a rear side of the (3-2)-th leg member with reference to a state in which the (3-1)-th leg member is disposed in parallel to a vertical direction, and extending in the vertical direction.

According to another embodiment, the leg mounted device may further include a knee mounted device coupled to the third leg part, which surrounds a knee of the user, and which adjusts a degree, by which the knee of the user is surrounded.

According to another embodiment, the knee mounted device may include an extension member coupled to the third leg part and extending from the third leg part to the knee of the user, an adjustment member coupled to the extension member to be moved along an extension direction of the extension member and an opposite direction to the extension direction of the extension member, a rotary member disposed on a side of the adjustment member, which is close to the knee of the user, and coupled to be rotatable with respect to the adjustment member, and a knee cover member coupled to the rotary member and which surrounds the knee of the user.

According to another embodiment, the knee mounted device may further include a locking member which fixes the adjustment to a specific location of the extension member.

According to another embodiment, the knee mounted device may further include an elastic member disposed between the adjustment member and the rotary member and elastically supporting the rotary member with respect to the adjustment member.

According to another embodiment, the extension member may include a saw-tooth area having a plurality of saw-teeth, and the adjustment member may be disposed in the saw-tooth area of the extension member and is configured such that a movement thereof in the extension direction and the opposite direction is obstructed by the saw-teeth.

According to another embodiment, the waist mounted device may further include a pelvis support member surrounding a pelvis of the user and connected to the leg mounted device, an abdomen support member located on a front side of the pelvis support member and to which the control device is coupled, and a strap member connecting the pelvis support member and the abdomen support member, and a length of which is adjustable such that the pelvis support member and the abdomen support member are adhered to the user when the user wears the waist mounted device.

According to another embodiment, the strap member may include a first strap connected to the pelvis support member, a second strap connected to the abdomen support member, and a buckle coupling the first strap and the second strap such that the first strap and the second strap are separable.

According to another embodiment, the walking assisting apparatus may further include a gripper protruding to a rear side of the leg mounted device and including a hole that is penetrated in one direction.

According to another embodiment, the support may include a support member extending downwards and contacting the ground surface, a knob member protruding forwards from the support member, and a cuff member provided on an upper side of the support member and surrounding a forearm of the user.

According to another embodiment, a groove opened downwards to house at least a portion of an upper area of the cuff member may be formed on a lower side of the connector.

According to another embodiment, the walking assisting apparatus may further include a back mounted device coupled to an upper side of the waist mounted device and which supports a back of the user.

According to another embodiment, the control device may include a controller which controls an operation of the leg mounted device, and a battery which supplies electric power to the leg mounted device.

BRIEF DESCRIPTION OF THE DRAWINGS

The above and other objects, features and advantages of embodiments of the present disclosure will be more apparent from the following detailed description taken in conjunction with the accompanying drawings, in which.

DETAILED DESCRIPTION OF ILLUSTRATIVE EMBODIMENTS

Figure 1:
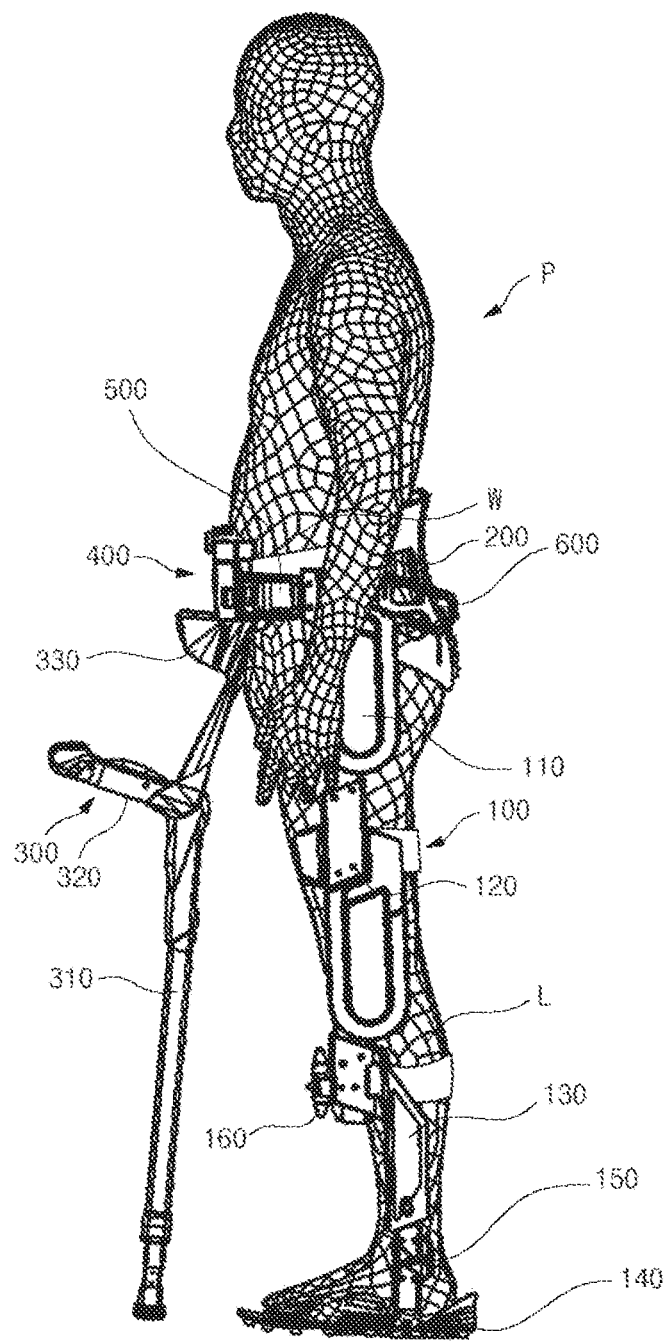
FIG. 1 is a view illustrating a state, in which a user wears a walking assisting apparatus according to an embodiment of the present disclosure, when viewed from a lateral side.

Hereinafter, some embodiments of the present disclosure will be described in detail with reference to the exemplary drawings. In providing reference numerals to the constituent elements of the drawings, the same elements may have the same reference numerals even if they are displayed on different drawings. Further, in the following description of the present disclosure, a detailed description of known functions and configurations incorporated herein will be omitted when it may make the subject matter of the present disclosure rather unclear.

Walking Assisting Apparatus

Figure 2:
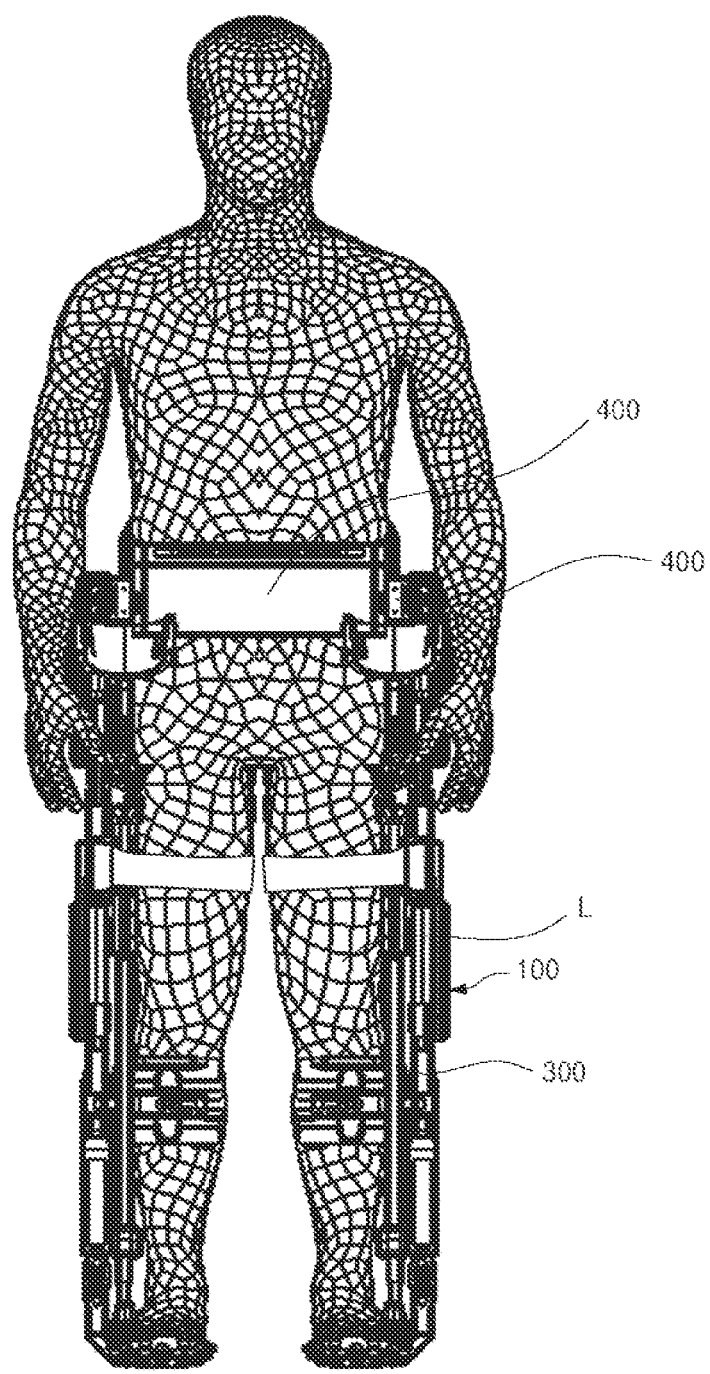
FIG. 2 is a view illustrating a state, in which a user wears a walking assisting apparatus according to an embodiment of the present disclosure, when viewed from a front side.
Figure 3:
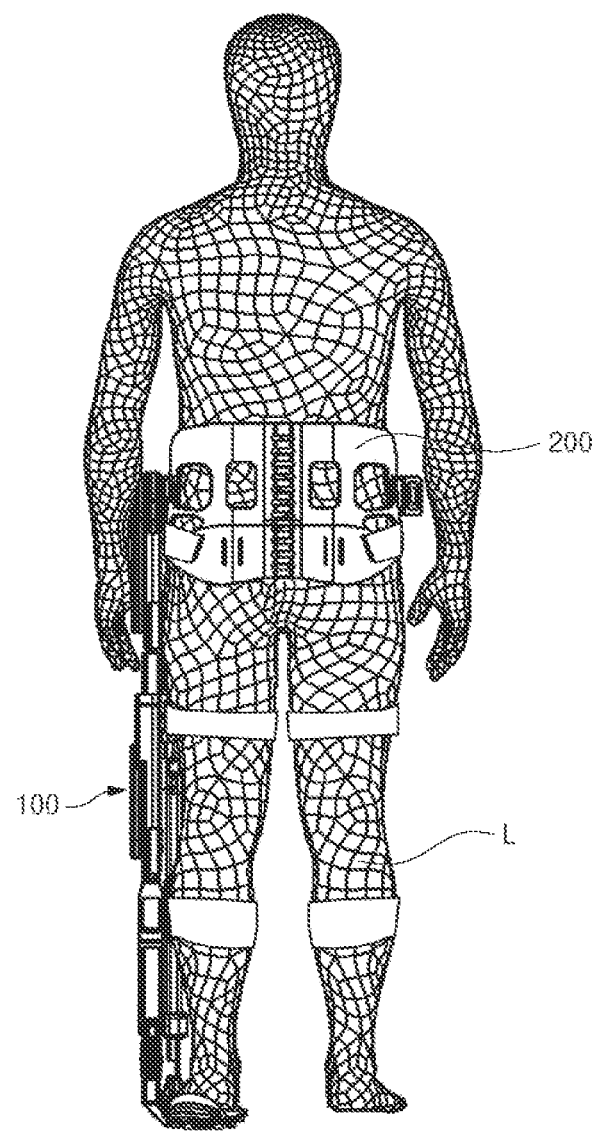
FIG. 3 is a view illustrating a state, in which a user wears a walking assisting apparatus according to an embodiment of the present disclosure, when viewed from a rear side.

A walking assisting apparatus according to an embodiment of the present disclosure is a walking assisting apparatus that is mounted on a body of a user "P" to assist walking of the user "P". FIG. 1 is a view illustrating a state, in which a user wears a walking assisting apparatus according to an embodiment of the present disclosure, when viewed from a lateral side. FIG. 2 is a view illustrating a state, in which a user wears a walking assisting apparatus according to an embodiment of the present disclosure, when viewed from a front side. FIG. 3 is a view illustrating a state, in which a user wears a walking assisting apparatus according to an embodiment of the present disclosure, when viewed from a rear side.

As illustrated in FIG. 1, the walking assisting apparatus according to the embodiment of the present disclosure may include a leg mounted device 100, a waist mounted device 200, a support 300, a control device 400, and a connector 500. The leg mounted device 100 may be mounted on a leg "L" of a user "P" to assist walking of the user "P". The waist mounted device 200 is provided on an upper side of the leg mounted device 100, and may be provided to be mounted on a waist "W" of the user "P".

The support 300 may be located on a front side of the leg mounted device 100. Furthermore, the support 300 may be configured to contact a ground surface. The support 300 may support the connector 500, which will be described below, with respect to the ground surface as it contacts the ground surface. The support 300 may be configured to be attachable to and detachable from the connector 500. The support 300 may be understood as a kind of a clutch.

The control device 400 may be coupled to a front side of the waist mounted device 200, and may be electrically connected to the leg mounted device 100 to control the leg mounted device 100.

The connector 500 may connect the control device 400 and the leg mounted device 100, and may detachably house the support 300. As an example, the connector 500 may detachably house an upper side of the support 300. As the support 300 detachably houses the connector 500, the user may use the support 300 as a unit for assisting walking after the support 300 is separated from the connector 500 while walking, and may use the support 300 as a unit for supporting the walking assisting apparatus, including the connector 500, by housing the support 300 in the connector 500 during stop.

According to embodiments of the present disclosure, because the control device 400 including a battery 420 (see FIG. 4) is located on the front side and the center of weight of the walking assisting apparatus is located on the front side, the user may be prevented from falling down.

Furthermore, according to embodiments of the present disclosure, because the support 300 may be connected to the connector 500 such that the support 500 supports the walking assisting apparatus and the body, a burden of a load applied to the user "P" may be reduced.

First Leg Part 110 and Second Leg Part 120

Figure 4:
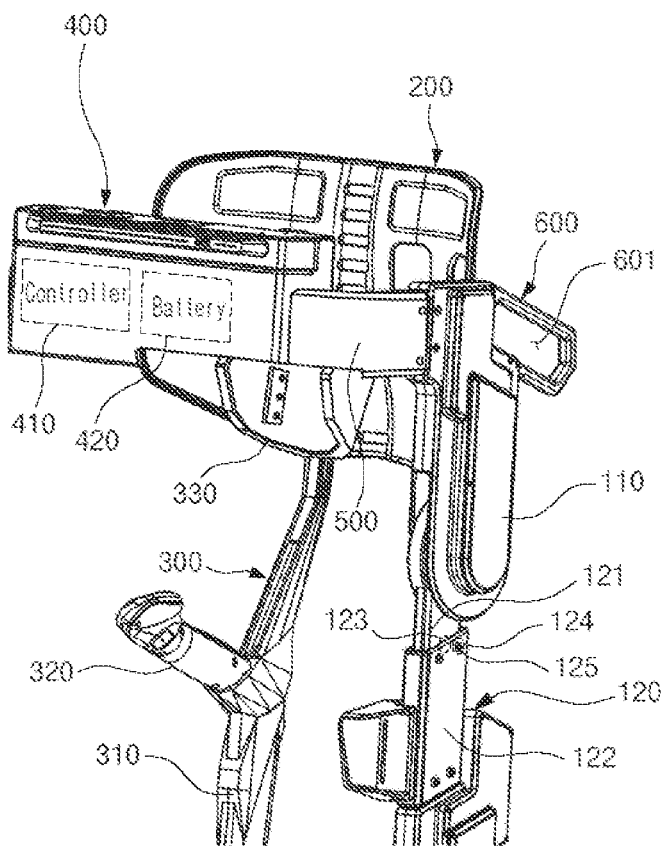
FIG. 4 is an enlarged view illustrating an upper side of a walking assisting apparatus according to an embodiment of the present disclosure.

FIG. 4 is an enlarged view illustrating an upper side of a walking assisting apparatus according to an embodiment of the present disclosure. As illustrated in FIG. 4, the leg mounted device 100 may include the first leg part no and the second leg part 120.

The first leg part no may be coupled to the waist mounted device 200 and may extend downwards. The second leg part 120 may be located on a lower side of the first leg part 110, a length of the second leg part 120 may be adjusted, and may be connected to the first leg part 110 such that the second leg part 120 and the first leg part 110 are rotated with respect to each other. As the length of the second leg part 120 may be adjusted, the leg mounted device 100 may be adjusted according to the height of the user "P".

In detail, in order to adjust the length of the second leg part 120, the second leg part 120 may include a (2-1)-th leg member 121 and a (2-2)-th leg member 122. The (2-1)-th leg member 121 may be connected to the first leg part 110 to be rotatable, and may extend downwards from the first leg part 110. The (2-2)-th leg member 122 is configured to surround the (2-1)-th leg member 121, and an extent of an area of the (2-2)-th leg member 122, which overlaps the (2-1)-th leg member 121, may be varied. As an example, the (2-1)-th leg member 121 is inserted into the (2-2)-th leg member 122, and as a degree, by which the (2-1)-th leg member 121 is inserted, varies, the extent of the area, in which the (2-1)-th leg member 121 and the (2-2)-th leg member 122 overlap each other, may vary.

The (2-1)-th leg member 121 may include a first hole 123 that is penetrated in one direction. The (2-2)-th leg member 122 may include a second hole 124. As the (2-2)-th leg member 122 is moved in a vertical direction, the second hole 124 may be disposed at a location that overlaps the first hole 123 when viewed along one direction. In order to vary the extent of the area, in which the (2-1)-th leg member 121 and the (2-2)-th leg member 122 overlap each other, at least any one of the number of the first hole 123 and the second hole 124 may be plural.

The second leg part 120 may further include a fixing member 125. The fixing member 125 may pass through the second hole 124 and the first hole 123, and may fix the (2-2)-th leg member 122 to a specific location of the (2-1)-th leg member 121. The fixing member may be a bolt and nut structure, and may be a pin structure.

Third Leg Part 130

Figure 5:
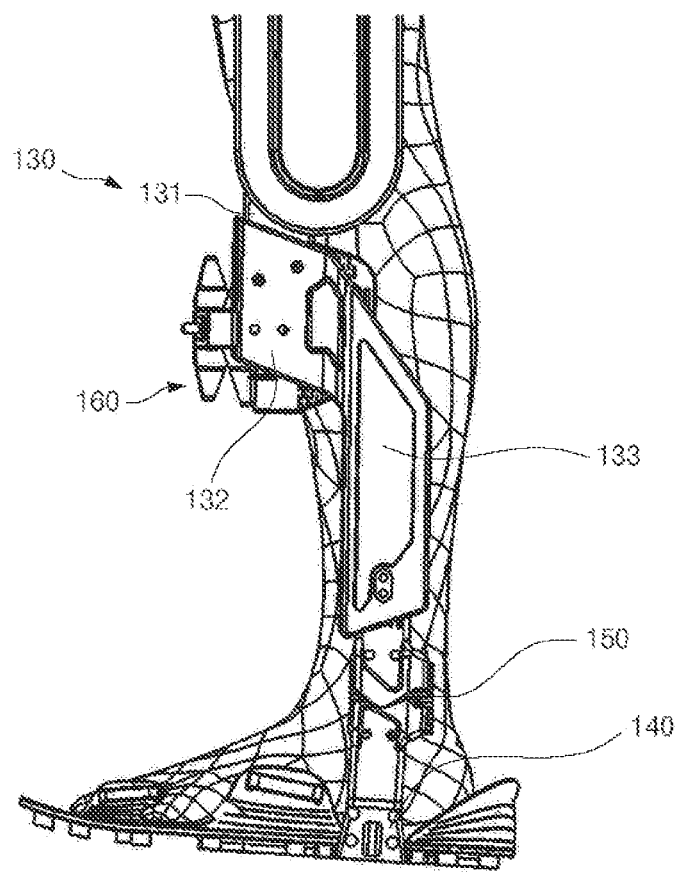
FIG. 5 is an enlarged view illustrating a lower side of a walking assisting apparatus according to an embodiment of the present disclosure.

FIG. 5 is an enlarged view illustrating a lower side of a walking assisting apparatus according to an embodiment of the present disclosure. As illustrated in FIGS. 1 and 5, the leg mounted device wo may further include the third leg part 130.

The third leg part 130 may be located on a lower side of the second leg part 120, a length of the third leg part 130 may be adjusted, and the third leg part 130 may be connected to the second leg part 120 such that the third leg part 130 and the second leg part 120 are rotated with respect to each other. The above description of the scheme of adjusting a length of the second leg part 120 may be applied to the third leg part 130 in the same way.

In detail, the third leg part 130 may include a (3-1)-th leg member 131, a (3-2)-th leg member 132, and a (3-3)-th leg member 133. The (3-1)-th leg member 131 may be connected to the second leg part 120 to be rotatable, and may extend downwards from the second leg part 120. The (3-2)-th leg member 132 is configured to surround the (3-1)-th leg member 131, and an extent of an area of the (3-2)-th leg member 132, which overlaps the (3-1)-th leg member 131, may be varied. The (3-3)-th leg member 133 may be connected to the (3-2)-th leg member 132, and may be disposed on a rear side of the (3-2)-th leg member 132 with reference to a state, in which the (3-1)-th leg member 131 is disposed in parallel in a vertical direction, and may extend in a vertical direction. This may be understood as the (3-3)-th leg member 133 being offset with the (3-2)-th leg member 132 in a forward/rearward direction.

That is, according to embodiments of the present disclosure, due to the (3-3)-th leg member 133 disposed on a rear side of the (3-2)-th leg member 132, the (3-2)-th leg member 132 located close to a knee joint of the user "P" and the (3-3)-th leg member 133 located close to a leg joint of the user "P", may not be disposed on the same vertical axis. Accordingly, because the center of weight of the walking assisting apparatus faces the front side due to the (3-2)-th leg member 132 located on the relatively front side and the components connected to an upper side thereof, a possibility of the user "P" falling rearwards may be solved and a problem of a psychical anxiety of the user "P" may be solved.

Foot Seated Part 140 and Foot Joint Part 150

The leg mounted device wo may further include the foot seated part 140 and the foot joint part 150. The foot seated part 140 may be configured such that a foot of the user "P" is seated thereon. The foot seated part 140 may be located on a lower side of the third leg part 130, and may be connected to the third leg part 130 to be rotatable. As an example, the foot seated part 140 may be formed to be rotatable in a range of −10 degrees to 10 degrees with respect to a direction that is perpendicular to the third leg part 130.

The foot joint part 150 may be configured such that the third leg part 130 is elastically supported with respect to the foot seated part 140. As an example, the foot joint part 150 may be a spring. In more detail, the foot joint part 150 may include a first spring and a second spring. The first spring may be a spring for dorsiflexion, and the second spring may be a spring for plantar flexion.

Then, the spring constants of the first and second springs may be different such that dorsiflexion may be caused in the user "P" in a swing phase.

As an example, the spring constant of the first spring may be smaller than the spring constant of the second spring. This causes dorsiflexion in the foot seated part 140 in the swing phase, and thus the user "P" may walk while the foot seated part 140 is not interfered by the ground surface. Further, as an example, the foot seated part 140 may be in a dorsiflexion state of 2.5 degrees in a neutral state.

Knee Mounted Device 160

Figure 6:
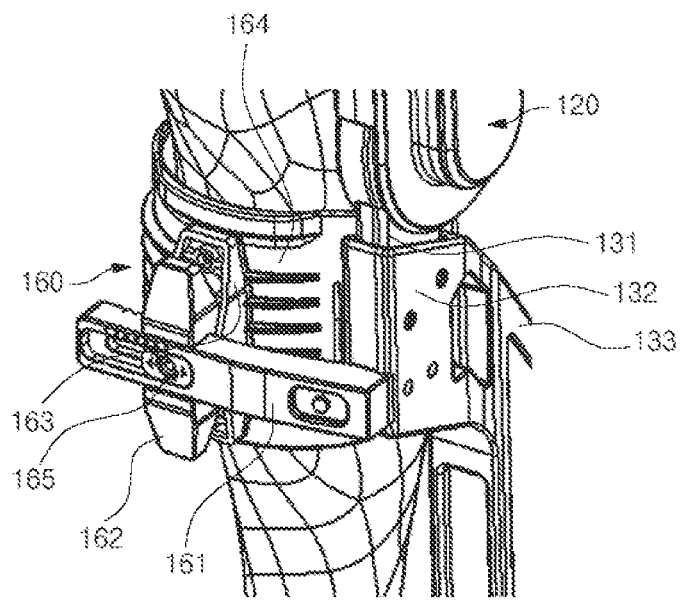
FIG. 6 is an enlarged view illustrating a knee mounted device of a walking assisting apparatus according to an embodiment of the present disclosure.
Figure 7:
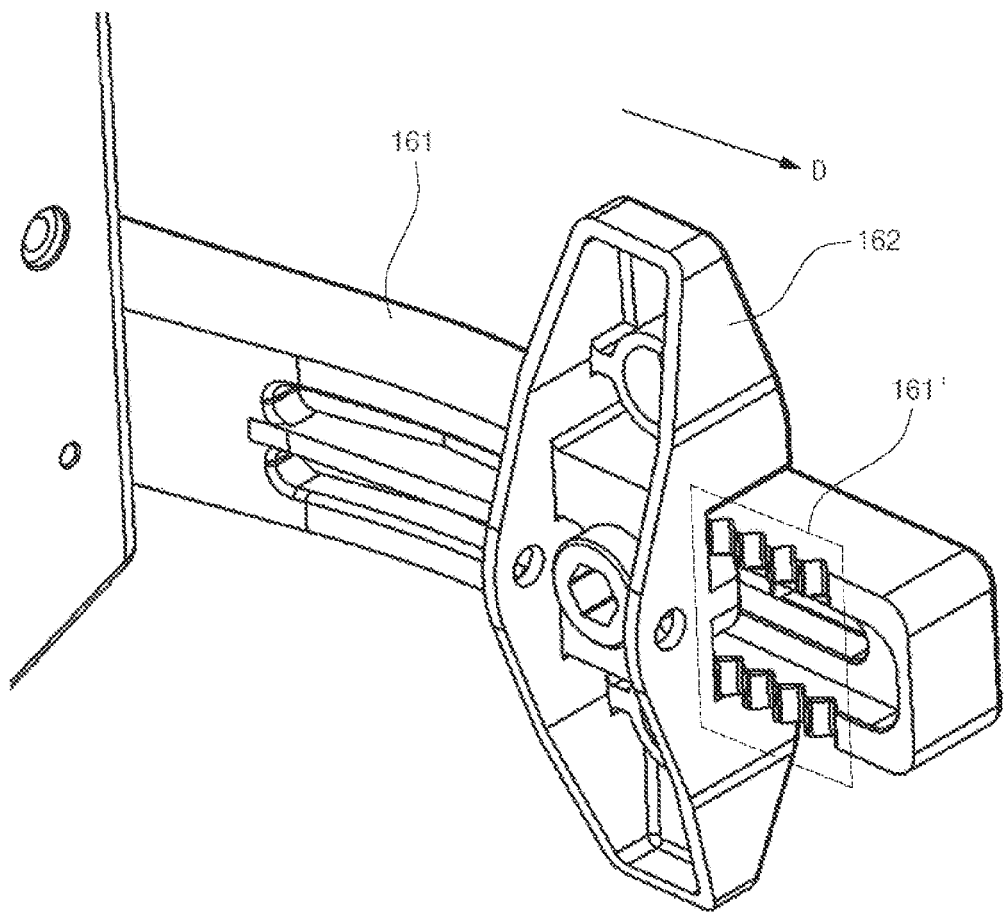
FIG. 7 is a view illustrating a state of an extension member and an adjustment member of the knee mounted device of FIG. 6, when viewed from another direction.
Figure 8:
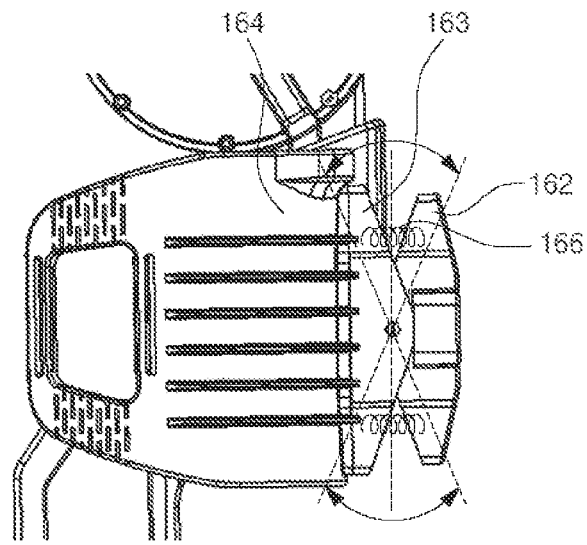
FIG. 8 is a view illustrating a state of an adjustment member, a rotary member, a knee cover member, and an elastic member of the knee mounted device of FIG. 6, when viewed from another direction.

FIG. 6 is an enlarged view illustrating a knee mounted device of a walking assisting apparatus according to an embodiment of the present disclosure. FIG. 7 is a view illustrating a state of an extension member and an adjustment member of the knee mounted device of FIG. 6, when viewed from another direction. FIG. 8 is a view illustrating a state of an adjustment member, a rotary member, a knee cover member, and an elastic member of the knee mounted device of FIG. 6, when viewed from another direction. Hereinafter, the knee mounted device will be described in detail with reference to FIGS. 6 to 8.

The leg mounted device wo may further include the knee mounted device 160. The knee mounted device 160 may be coupled to the third leg part 130, and may be configured to surround the knee of the user "P". The knee mounted device 160 may adjust a degree, by which the knee of the user "P" is surrounded. The knee mounted device 160 may be mounted according to the state of the knee joint of the user "P", and may prevent a valgus and a varus of the knee of the user "P".

As an example, the knee mounted device 160 may include an extension member 161, an adjustment member 162, a rotary member 163, and a knee cover member 164. The extension member 161 may be coupled to the third leg part 130, and may extend from the third leg part 130 to the knee of the user "P". The adjustment member 162 may be coupled to the extension member 161 to be moved along an extension direction D of the extension member 161 and an opposite direction thereto. The rotary member 163 may be disposed on a side of the adjustment member 162, which is close to the knee of the user "P", and may be coupled to the adjustment member 162 to be rotatable. The knee cover member 164 may be coupled to the rotary member 163, and may be configured to surround the knee of the user "P".

The knee mounted device 160 may further include a locking member 165. The locking member 165 may fix the adjustment member 162 to a specific location of the extension member 161. Further, the knee mounted device 160 may further include an elastic member 166. The elastic member 166 may be disposed between the adjustment member 162 and the rotary member 163, and may elastically support the rotary member 163 with respect to the adjustment member 162. Due to the elastic member 166, the knee of the user "P" may be supported more stably.

The extension member 161 may include a saw-tooth area 161' having a plurality of saw-teeth. The adjustment member 162 may be disposed in the saw-tooth area 161' of the extension member 161, and may be configured to be prevented from being moved in the extension direction D and the opposite direction thereto, due to the saw-teeth. By using the shapes of the extension member 161 and the adjustment member 162, the knee mounted device 160 may be mounted on the user "P" according to the size of the knee of the user "P".

Waist Mounted Device 200

Figure 9:
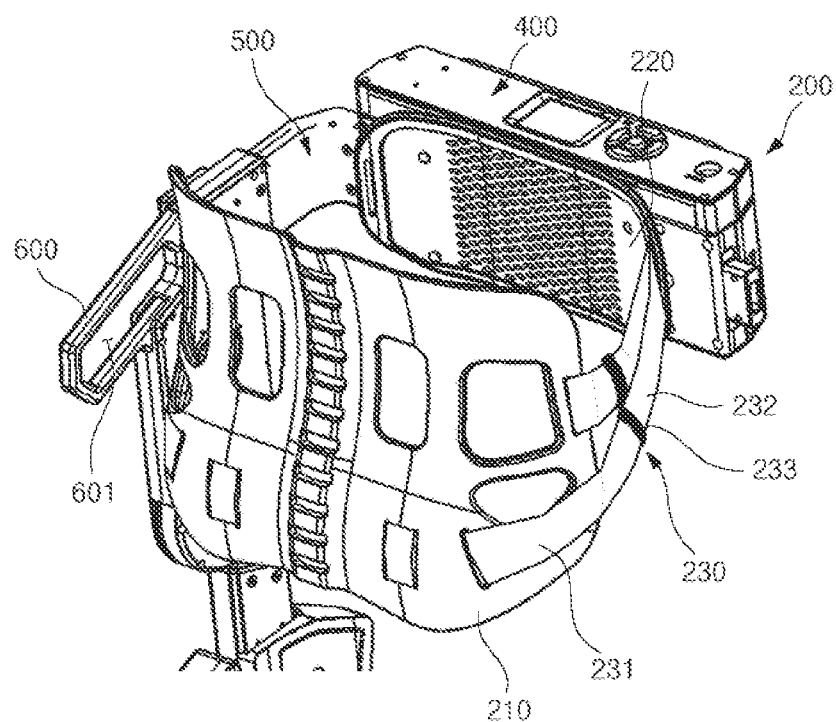
FIG. 9 is an enlarged view illustrating a waist mounted device of a walking assisting apparatus according to an embodiment of the present disclosure.

FIG. 9 is an enlarged view illustrating a waist mounted device of a walking assisting apparatus according to an embodiment of the present disclosure. As illustrated in FIG. 9, the waist mounted device 200 may include a pelvis support member 210, an abdomen support member 220, and a strap member 230.

The pelvis support member 210 may be configured to surround the pelvis of the user "P", and may be connected to the leg mounted device 100 (see FIG. 1 and the like). The abdomen support member 220 may be located on a front side of the pelvis support member 210, and the control device 400 may be coupled to a front surface thereof.

The strap member 230 may connect the pelvis support member 210 and the abdomen support member 220. A length of the strap member 230 may be adjusted such that the pelvis support member 210 and the abdomen support member 220 are adhered to the user "P" when the user "P" wears the waist mounted device 200.

As an example, the strap member 230 may include a first strap 231, a second strap 232, and a buckle 233. The first strap 231 may be connected to the pelvis support member 210 and the second strap 232 may be connected to the abdomen support member 220. The buckle 233 may couple the first strap 231 and the second strap 232 such that the first strap 231 and the second strap 232 may be separated from each other. Furthermore, the buckle 233 may be configured to adjust the lengths of the first strap 231 and the second strap 232. The strap member 230 may be understood as a form such as a kind of a bag strap.

Connector 500

As illustrated in FIG. 4, the walking assisting apparatus according to an embodiment of the present disclosure may include the connector 500. The connector 500 may connect the control device 400 and the leg mounted device 100. Furthermore, the connector 500 may house the support 300. The statement that the support 300 is housed means that the support 300 is housed such that one side of the support 300 contacts the ground surface and another side of the support 300 is connected to the connector 500 in order to support the walking assisting apparatus by the support 300 with respect to the ground surface. In order to describe the structure of housing the support 300 by the connector 500 in detail, the shape of the support 300 will be described in detail first.

Support 300

Referring to FIG. 1, the support 300 may include a support member 310, a knob member 320, and a cuff member 330. The support member 310 may extend downward and be configured to contact the ground surface. The knob member 320 may protrude forward from the support member 310. The knob member 320 may be configured to be gripped by a hand of the user "P". The cuff member 330 may be provided on an upper side of the support member 310, and may be configured to surround a forearm of the user "P". In a state in which walking is assisted by using the support 300, the forearm of the user "P" may be supported by the cuff member, and walking may be assisted by moving the support 300 while the knob member 320 is gripped by a hand.

Then, when the user "P" moves while always gripping the support 300, a load may be continuously applied to an arm of the user "P" and the two arms may not be free as well. Accordingly, when the user "P" does not need to move, the support 300 may be housed in the connector 500 to support the walking assisting apparatus. Hereinafter, an example of the method will be described in detail.

Figure 10:
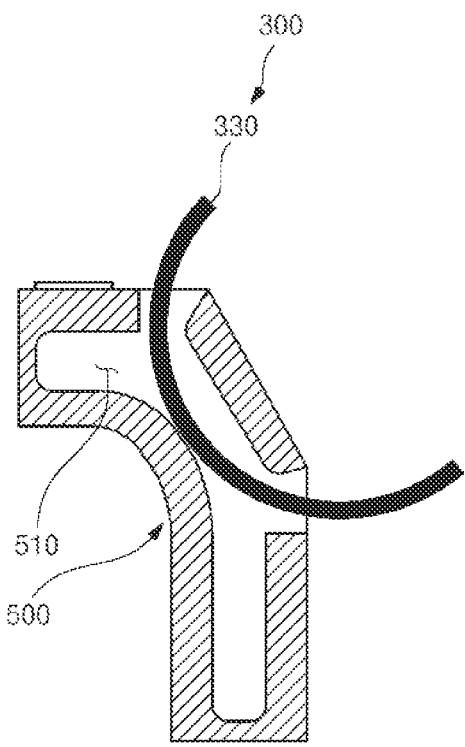
FIG. 10 is a cross-sectional view illustrating a state of a connector according to an embodiment of the present disclosure, when viewed from a lower side.

FIG. 10 is a cross-sectional view illustrating a state of a connector according to an embodiment of the present disclosure, when viewed from a lower side. As illustrated in FIG. 10, a groove 510 may be formed on a lower side of the connector 500. The groove 510 may be opened toward the lower side to house at least a portion of an upper area of the cuff member 330. For example, the connector 500 may be understood as a form, in which the connector 500 is positioned on the cuff member. Due to the form, when the user "P" does not need to move, the support 300 may be housed in the connector 500 to support the walking assisting apparatus.

Control Device 400

As illustrated in FIG. 4, the control device 400 may include a controller 410 and a battery 420. The controller 410 may be configured to control an operation of the leg mounted device 100. The battery 420 may include a battery that is configured to supply electric power to the leg mounted device 100. Because the control device 400 has a heavy weight, the user "P" may be prevented from falling down rearward as the control device 400 is disposed on the front side.

The control device 400 may further include a processor and a memory. The processor may include a microprocessor such as a field programmable gate array (FPGA), an application specific integrated circuit (ASIC), or a central processing unit (CPU). The memory may store control instructions that are basic in generating instructions for an operation of the leg mounted device 100 by the processor. The memory may be a data storage such as a hard disk drive (HDD), a solid state drive (SSD), a volatile medium, and a nonvolatile medium.

Gripper 600

As illustrated in FIG. 4, the walking assisting apparatus according to an embodiment of the present disclosure may include the gripper 600. The gripper 600 may protrude to the rear side of the leg mounted device 100, and may include a hole 601 that is penetrated in one direction. An assister who assists walking of the user "P" may grip the gripper 600 by inserting a hand into the hole 601. The assister may assist walking of the user "P" while gripping the gripper 600, or may allow the user "P" to escape from a dangerous situation through the gripper 600 when the user "P" is in the dangerous situation.

Back Mounted Device 700

Figure 11:
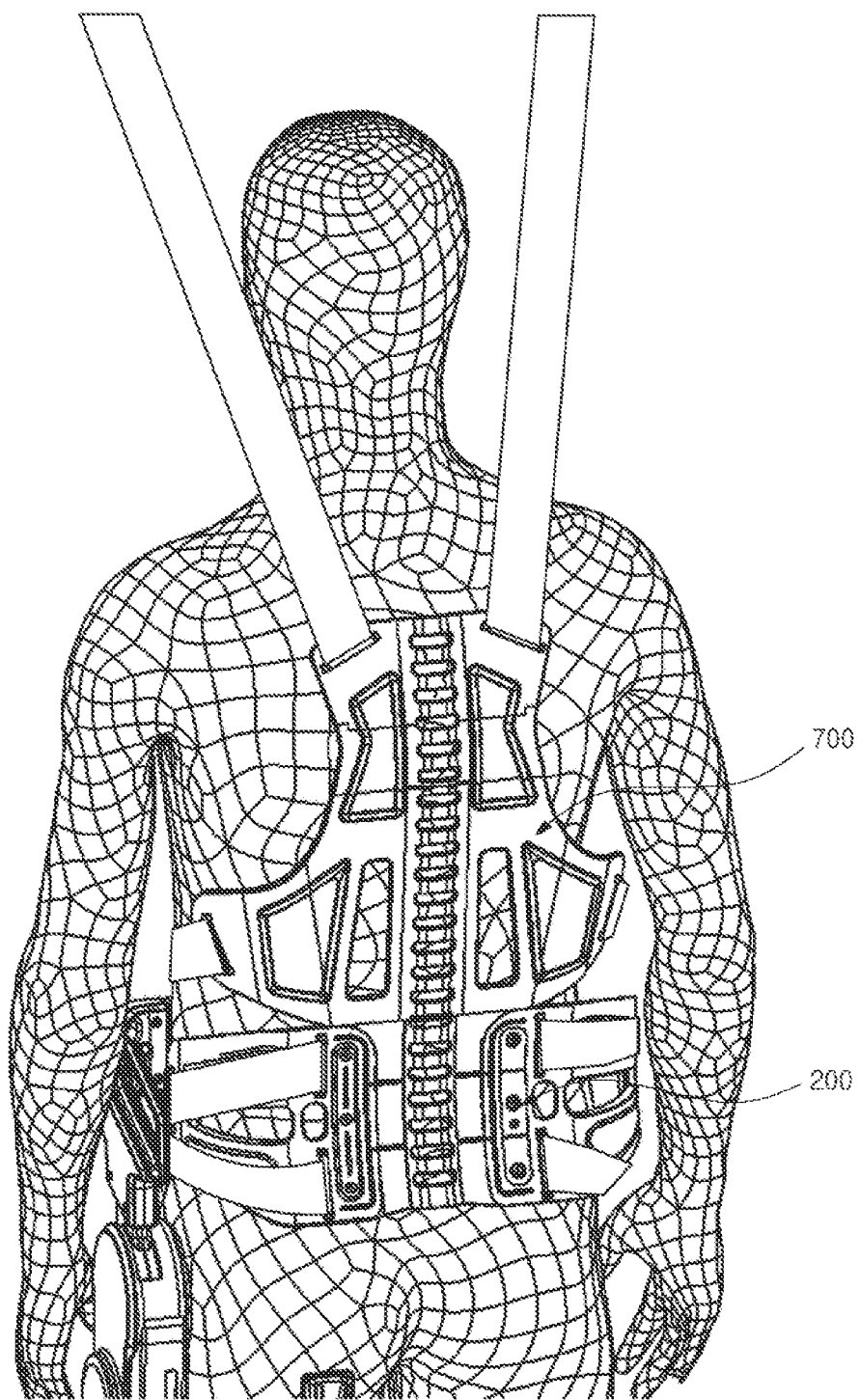
FIG. 11 is an enlarged view illustrating a back mounted device of a walking assisting apparatus according to an embodiment of the present disclosure.

FIG. 11 is an enlarged view illustrating a back mounted device of a walking assisting apparatus according to an embodiment of the present disclosure. As illustrated in FIG. 11, the walking assisting apparatus according to an embodiment of the present disclosure may further include the back mounted device 700. The back mounted device 700 may be coupled to an upper side of the waist mounted device 200, and may be configured to support the back of the user "P". The back mounted device 700 may be separated from the waist mounted device 200 when there is no need to support the back.

According to embodiments of the present disclosure, the control device including the battery may be located on the front side and the user may be prevented from falling down rearwards.

In addition, according to embodiments of the present disclosure, because the apparatus may be supported by a clutch by holding the clutch in the apparatus, a burden of a load applied to the user may be reduced.

The above description is a simple exemplification of the technical spirits of the present disclosure, and the present disclosure may be variously corrected and modified by those skilled in the art to which the present disclosure pertains without departing from the essential features of the present disclosure. Accordingly, the embodiments disclosed in the present disclosure are not provided to limit the technical spirits of the present disclosure but provided to describe the present disclosure, and the scope of the technical spirits of the present disclosure is not limited by the embodiments. Accordingly, the technical scope of the present disclosure should be construed by the attached claims and all the technical spirits within the equivalent ranges fall within the scope of the present disclosure.

What is claimed is:

1. A walking assisting apparatus, the apparatus comprising:
    a leg mounted device configured to be mounted on a leg of a user to assist walking of the user;
    a waist mounted device provided on an upper side of the leg mounted device and configured to be mounted on a waist of the user;
    a support located on a front side of the leg mounted device and configured to contact a ground surface;
    a control device coupled to a front side of the waist mounted device, electrically connected to the leg mounted device, and configured to control the leg mounted device; and
    a connector connecting the control device and the leg mounted device to detachably house the support.

2. The apparatus of claim 1, wherein the leg mounted device comprises:
    a first leg part configured to be coupled to the waist mounted device and extend downward toward the ground surface; and
    a second leg part located on a lower side of the first leg part and connected to the first leg part to be rotatable, a length of the second leg part being adjustable.

3. The apparatus of claim 2, wherein the leg mounted device further comprises a third leg part located on a lower side of the second leg part and connected to the second leg part to be rotatable, a length of the third leg part being adjustable.

4. The apparatus of claim 3, wherein the leg mounted device further comprises:
    a foot seated part located on a lower side of the third leg part, connected to the third leg part to be rotatable, and configured to allow a foot of the user to be seated thereon; and
    a foot joint part configured such that the third leg part is elastically supported on the foot seated part.

5. The apparatus of claim 3, wherein the third leg part further comprises:
    a (3-1)-th leg member connected to the second leg part and configured to be rotatable and extend downward from the second leg part;
    a (3-2)-th leg member surrounding the (3-1)-th leg member and configured such that an extent of an area that overlaps the (3-1)-th leg member is variable; and
    a (3-3)-th leg member connected to the (3-2)-th leg member, disposed on a rear side of the (3-2)-th leg member with reference to a state in which the (3-1)-th leg member is disposed in parallel to a vertical direction, and extending in the vertical direction.

6. The apparatus of claim 2, wherein the second leg part comprises:
    a (2-1)-th leg member connected to the first leg part to be rotatable and extending downward toward the ground surface from the first leg part; and
    a (2-2)-th leg member surrounding the (2-1)-th leg member and configured such that an extent of an area that overlaps the (2-1)-th leg member is variable.

7. The apparatus of claim 6, wherein:
    the (2-1)-th leg member comprises a first hole that is penetrated in one direction;
    the (2-2)-th leg member comprises a second hole that is disposed at a location that is configured to overlap the first hole when viewed from the one direction as the (2-2)-th leg member is moved along a vertical direction; and
    the second leg part further comprises a fixing member that passes through the second hole and the first hole and is configured to fix the (2-2)-th leg member to a specific location of the (2-1)-th leg member.

8. The apparatus of claim 1, wherein the waist mounted device further comprises:

a pelvis support member configured to surround a pelvis of the user and connected to the leg mounted device;

an abdomen support member located on a front side of the pelvis support member and to which the control device is coupled; and a strap member connecting the pelvis support member and the abdomen support member, wherein a length of the strap member is adjustable such that the pelvis support member and the abdomen support member can be adhered to the user when the user wears the waist mounted device.

9. The apparatus of claim 8, wherein the strap member comprises:
a first strap connected to the pelvis support member;
a second strap connected to the abdomen support member; and
a buckle coupling the first strap and the second strap such that the first strap and the second strap are separable.

10. The apparatus of claim 1, further comprising a gripper protruding toward a rear side of the leg mounted device, the gripper including a hole penetrated in one direction.

11. The apparatus of claim 1, wherein the support comprises:
a support member extending downwards and contacting the ground surface;
a knob member protruding forwards from the support member; and
a cuff member provided on an upper side of the support member and configured to surround a forearm of the user.

12. The apparatus of claim 11, further comprising a groove formed on a lower side of the connector, the groove being open downward to house at least a portion of an upper area of the cuff member.

13. The apparatus of claim 1, further comprising a back mounted device configured to be coupled to an upper side of the waist mounted device and configured to support a back of the user.

14. The apparatus of claim 1, wherein the control device comprises:
a controller configured to control an operation of the leg mounted device; and
a battery configured to supply electric power to the leg mounted device.

15. A walking assisting apparatus, the apparatus comprising:
a waist mounted device configured to be mounted on a waist of a user;
a leg mounted device provided on a lower side of the waist mounted device and configured to be mounted on a leg of the user to assist walking of the user, wherein the leg mounted device comprises:
a first leg part coupled to the waist mounted device and extending downward toward a ground surface;
a second leg part located on a lower side of the first leg part and connected to the first leg part to be rotatable, a length of the second leg part being adjustable;
a third leg part located on a lower side of the second leg part and connected to the second leg part to be rotatable, a length of the third leg part being adjustable; and
a knee mounted device coupled to the third leg part, configured to surround a knee of the user, and configured to adjust a degree by which the knee of the user is surrounded;
a support located on a front side of the leg mounted device and configured to contact the ground surface;
a control device coupled to a front side of the waist mounted device, electrically connected to the leg mounted device, and configured to control the leg mounted device; and
a connector connecting the control device and the leg mounted device to detachably house the support.

16. The apparatus of claim 15, wherein the knee mounted device comprises:
an extension member coupled to the third leg part and configured to extend from the third leg part to the knee of the user;
an adjustment member coupled to the extension member and configured to be moved along an extension direction of the extension member and an opposite direction to the extension direction of the extension member;
a rotary member disposed on a side of the adjustment member and coupled to be rotatable with respect to the adjustment member; and
a knee cover member coupled to the rotary member and configured to surround the knee of the user.

17. The apparatus of claim 16, wherein the knee mounted device further comprises a locking member configured to fix the adjustment member to a specific location of the extension member.

18. The apparatus of claim 16, wherein the knee mounted device further comprises an elastic member disposed between the adjustment member and the rotary member and elastically supporting the rotary member with respect to the adjustment member.

19. The apparatus of claim 16, wherein the extension member includes a saw-tooth area having a plurality of saw-teeth.

20. The apparatus of claim 19, wherein the adjustment member is disposed in the saw-tooth area of the extension member and wherein the saw-teeth are configured to obstruct a movement of the adjustment member in the extension direction and the opposite direction.

* * * * *